United States Patent [19]

Mariella, Jr. et al.

[11] Patent Number: 5,475,487
[45] Date of Patent: Dec. 12, 1995

[54] AQUEOUS CARRIER WAVEGUIDE IN A FLOW CYTOMETER

[75] Inventors: Raymond P. Mariella, Jr., Danville, Calif.; Gerrit van den Engh, Seattle, Wash.; M. Allen Northrup, Berkeley, Calif.

[73] Assignee: The Regents of the University of California, Oakland, Calif.

[21] Appl. No.: 230,077

[22] Filed: Apr. 20, 1994

[51] Int. Cl.⁶ .......................... G01N 15/02; G01N 21/00; G02B 6/20
[52] U.S. Cl. .......................... 356/336; 356/338; 356/339; 385/125; 250/574
[58] Field of Search .......................... 356/335–339, 356/343, 72; 250/574; 385/125, 12

[56] References Cited

U.S. PATENT DOCUMENTS

| | | | |
|---|---|---|---|
| 3,680,962 | 8/1972 | Hayakawa | 356/338 |
| 4,045,119 | 8/1977 | Eastgate | 385/125 |
| 4,659,218 | 4/1987 | de Lasa et al. | 356/335 |
| 4,662,749 | 5/1987 | Hatton et al. | 356/336 |
| 4,702,598 | 10/1987 | Bohmer | 356/343 |
| 4,877,966 | 10/1989 | Tomei et al. | 250/458.1 |
| 5,013,150 | 5/1991 | Watts et al. | 356/338 |
| 5,044,723 | 9/1991 | MacDonald | 385/12 |
| 5,191,388 | 3/1993 | Kilham | 356/335 |

Primary Examiner—Frank Gonzalez
Assistant Examiner—Jason D. Eisenberg
Attorney, Agent, or Firm—Henry P. Sartorio; John P. Wooldridge

[57] ABSTRACT

The liquid of a flow cytometer itself acts as an optical waveguide, thus transmitting the light to an optical filter/detector combination. This alternative apparatus and method for detecting scattered light in a flow cytometer is provided by a device which views and detects the light trapped within the optical waveguide formed by the flow stream. A fiber optic or other light collecting device is positioned within the flow stream. This provides enormous advantages over the standard light collection technique which uses a microscope objective. The signal-to-noise ratio is greatly increased over that for right-angle-scattered light collected by a microscope objective, and the alignment requirements are simplified.

18 Claims, 4 Drawing Sheets

AQUEOUS CARRIER WAVEGUIDE IN A FLOW CYTOMETER

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the detection of light scatter in a flow cytometer, and more specifically, it relates to the use of the flow stream of a flow cytometer as an optical waveguide.

2. Description of Related Art

Flow cytometry is a technique used to characterize and categorize biological cells and/or their contents, such as DNA, and record their distributions, including actual sorting of this biological material in some cases. The biological cells are present in an aqueous-based solution, even when the sample material is eluted from a polymer matrix, such as in sheath-flow detection in electrophoresis experiments. In flow cytometry, the experimenter shines one or more beams of light at the biological material in the aqueous stream and observes the elastically and inelastically scattered light. The inelastically scattered light which is of interest is usually just fluorescence. Variations in the cells or DNA cause variations in the scattered light and these variations allow the desired characterization and categorization. To quantify these variations, the scattered light must be collected. In general, less right angle scattered (RAS) light is produced than small angle scattered light. It is desirable to collect as much of the scattered light as possible in order to maximize the speed and sensitivity of the procedure.

In previously used flow cytometers, the right angle scattered light has been viewed perpendicularly to the liquid flow, typically using a high numerical aperture (NA) microscope objective lens or fiber optic. Highest quality microscope objectives have a "numerical aperture" of 0.6, which provides a subtended polar angle of $2\beta=37°$ (0.64 radians). Some of the difficulties associated with this approach include the very limited depth of field of high NA lenses, and the necessity to align precisely the exact focal point of the lens with the illuminated region of the flow stream.

SUMMARY OF THE INVENTION

It is an object of the present invention to provide a method and apparatus which uses the aqueous flow stream of a flow cytometer as an optical waveguide.

It is also an object of the invention to measure the scattered light trapped within the aqueous flow stream of a flow cytometer.

The present invention provides an alternative apparatus and method for detecting scattered light in a flow cytometer. In the invention, the liquid itself acts as an optical waveguide, thus transmitting the light to a detection scheme such as an optical filter/detector combination, possibly through a fiber-optic (FO) line. This offers enormous advantages over the standard light collection technique which uses a microscope objective. This new configuration for Flow Cytometry greatly increases the signal-to-noise ratio for right-angle-scattered (RAS) light and greatly eases the alignment requirements.

DETAILED DESCRIPTION OF THE INVENTION

Figure 1:
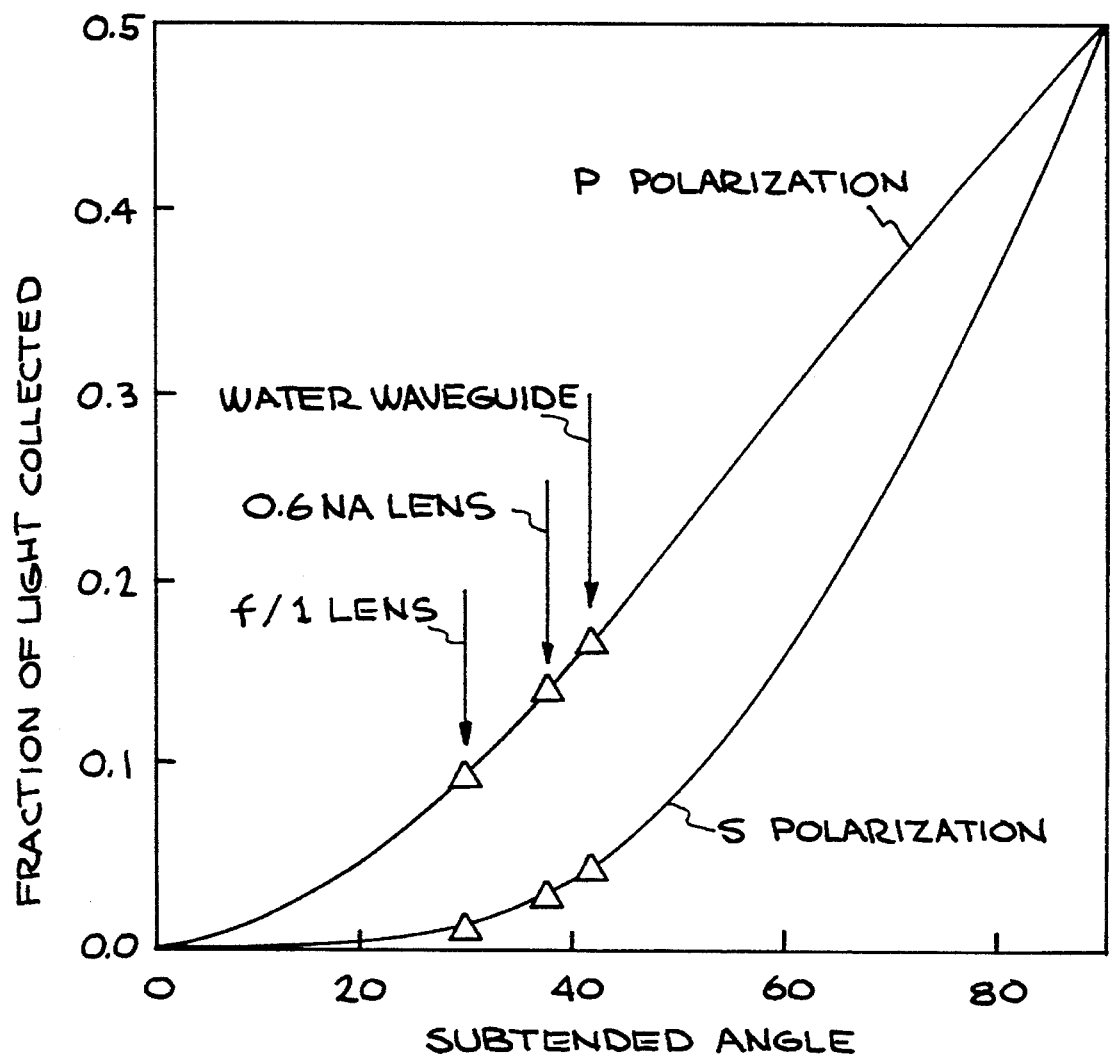
FIG. 1 is a plot of light collected versus subtended angle for S and P orientations of an electric-dipole emitter.

The excitation sources which are typically used in flow cytometers are linearly polarized lasers. For an electric dipole emitter, the intensity of scattered light is directly proportional to the square of $\sin(\theta)$, where $\theta$ is the angle away from the E-field vector; this is maximized for $\theta=90°$ (or $\pi/2$ radians). Thus, in order to maximize the collection of scattered light, the polarization of the laser should be adjusted so that the electric field is perpendicular to the viewing direction of the light detector. With the E-field polarization vector along the z axis, the maximum emission intensity is in the X-Y plane, and the emission intensity along the Z axis is nil. FIG. 1 is a plot of the fraction of light collected versus the subtended angle. Highest quality microscope objectives have a "numerical aperture" of 0.6, which provides a subtended polar angle of $2\beta=37°$ (0.64 radians). For both orthogonal polarizations, the best fraction for an optimized microscope objective with 0.6 numerical aperture is 14%. The best for the aqueous optical waveguide is 16%. For the worst-case polarization, the aqueous optical waveguide should collect only 4% versus about 2% for the 0.6 NA lens.

Figure 2:
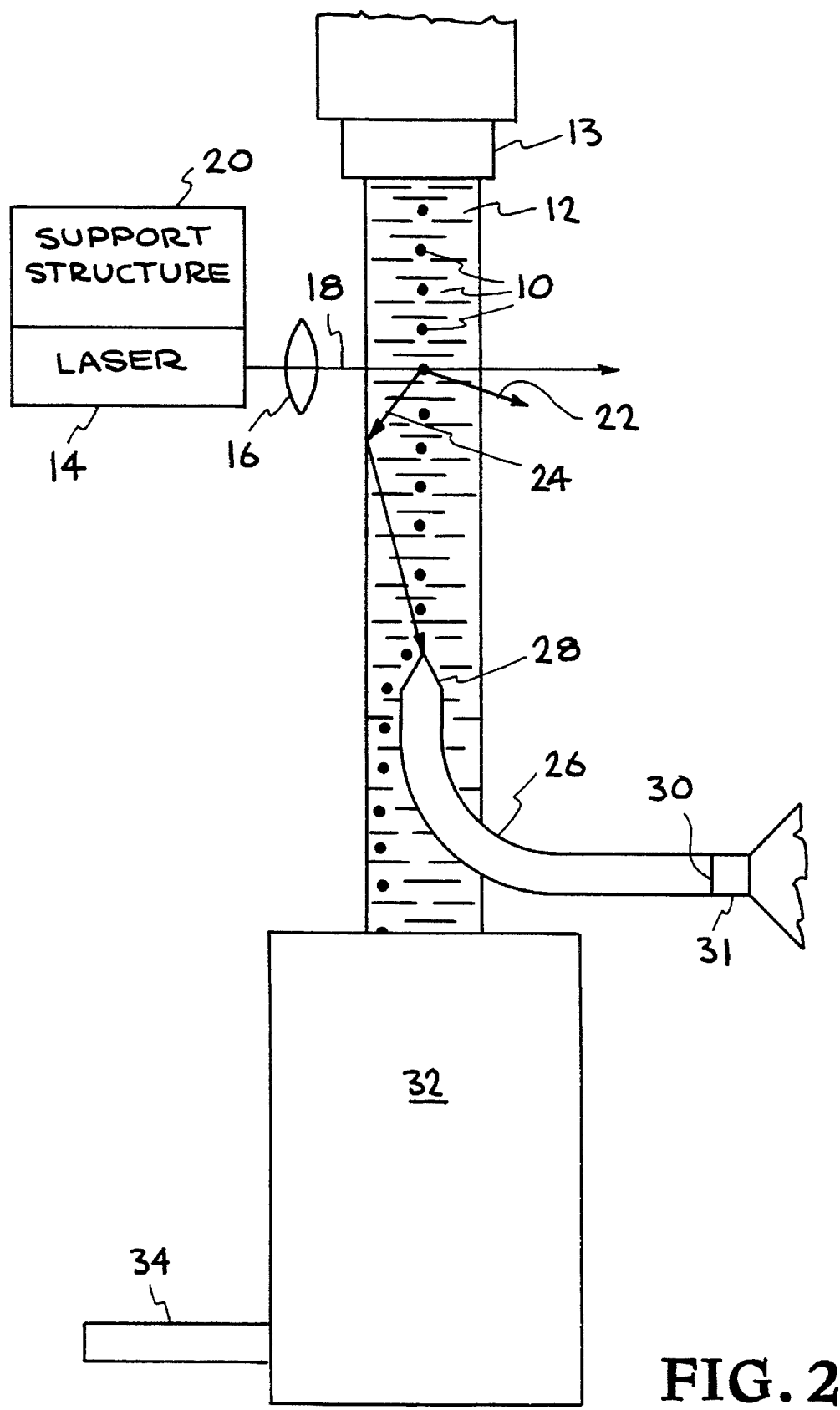
FIG. 2 is a schematic drawing of a diode-laser flow cytometer having a conical fiber.

FIG. 2 is a schematic drawing of a diode-laser flow cytometer having a tapered fiber. Cells 10 in an aqueous carrier 12 flow down through an orifice 13 to form a free stream. Orifice 13 may have a 50 μm inside diameter. A diode-laser 14 having a microlens 16 directs a laser beam 18 through aqueous carrier 12. Diode-laser 14 is rigidly held by a support structure 20. Diode-laser 14 may be replaced with a solid state laser, a gas laser, a dye laser or an arc lamp. When passing through laser beam 18, cells 10 simultaneously produce forward light scatter 22 and RAS signal 24. Aqueous carrier 12 guides RAS signal 24 into a fiber-optic 26 having a tapered end 28. RAS signal 24 is guided through fiber-optic 26 and out of interface 30 to a detector 31 which may comprise filter 29. Aqueous carrier 12 is collected by liquid collector 32 and guided to a liquid collection or disposal system (not shown) through channel 34.

In addition to collecting more light due to the larger subtended angle, one additional advantage to using the waveguide system rather than using the microscope objective is the relative insensitivity of the waveguide system to misalignments; the microscope objective has a limited depth of field and limited width of viewing plane (caused partially by apertures in the optical system). If the cells being illuminated are not at the exact focal point of the microscope objective, some of the scattered light will fail to reach the detector, but the waveguide system has no such sensitivity to cell position, since the angle for total internal reflection is not dependent upon position within the liquid stream. Similarly, one can illuminate the cells at several positions along the flow of the stream and still use just one light detection system at the end of a fiber.

An experiment was conducted to evaluate and compare the performance of collecting right angle scatter (RAS) light using the conventional prior art orthogonal (90°) scatter collection method, and the unconventional "instream" method of the invention that places a tapered-end fiber optic downstream of the flow stream/laser intersection point. The experiment used a Coherent model Innova 200® visible laser, set to the 457.9 nm line in the $TEM_{00}$ mode. The only modification to the "standard" optical train of a MoFlo cytometer was the addition of a Melles-Griot ½-wave retardation plate, so that the effects of polarization on scatter signals could be determined. The laser beam diameter at the flow stream/laser intersection was approximately 25 μm, and its profile was circular. The excitation laser beam is normally 90° with respect to the aqueous flow stream; however, the invention is operable at smaller angles.

The "conventional" orthogonal scatter collection optics consisted of a high numerical aperture, long working distance microscope lens (32×) and an N.A. of 0.60. The lens was followed by a 1-mm diameter pinhole at the focal plane and another lens to image the pinhole onto the approximately 5.1-mm$^2$ diameter active area of an EG&G HAD 1100A series high speed PIN-photodiode/Op-amp module.

The "unconventional" scatter collector was made from a 400-μm-core-diameter fiber optic, manufactured by the 3M company, that was conically polished at one end to a 26° included angle, and flat polished at the other. The fiber has been installed into a fixture, and attached to X-Y translators that allow the experimenter to position the fiber accurately into the flow stream. The flat polished end of the fiber is coupled to another EG&G HAD 1100A series high speed PIN-photodiode/Op-amp module with a 1-megohm feedback resistor that has been matched and calibrated to have the same responsivity and gain bandwidth as the detector used in the "conventional" scatter collector. The fiber is positioned concentrically with the flow stream at about 1 cm below the flowstream/laser ceramic flow nozzle.

Based on the experimental data collected, the fiber-based scatter detector collected the scatter data 7 to 10 times more effectively than the conventional right-angle system used on the current MoFlo system. When the ½-waveplate was rotated through 360° there was no noticeable change in the output signals to either of the detector systems. The polarization of the laser was found to be in the "P" vector and orthogonal to the table. As the laser power was varied between 300 mW and 1 watt, the baseline of the conventional detector's signal increased approximately 4 mV or about 0.003 % of the peak output signal. The fiber detector showed no increase, although the typical baseline amplifier noise is 1 mV; all measurements were taken without external gain. It should be noted also that the PIN diode detectors were not being used at their peak responsivity of 0.50 Amps/Watt at 950 nm, but were down to 0.21 Amps/Watt at 458 nm.

In our experiment, the electric field polarization was perpendicular to the microscope objective and directed toward the optical waveguide. The most likely explanation for the unexpectedly good performance of the waveguide light collection versus the microscope objective is the insensitivity of the waveguide system to depth of field and other practical aspects of alignment and imaging of the microscope objective.

By using the unconfined aqueous flow stream of a cytometer as an optical waveguide, approximately 17% of the solid angles are captured. This nominal increase over the standard high numerical aperture lens is augmented by the fact that all of the scattered light is trapped, according to its angle of propagation, not its position. There is no "focal point" for this configuration. Alignment simply requires aligning the light source onto the flow stream; the liquid optical waveguide is then automatically "aligned". The flow rates should be adjusted to form a smooth stream. This approach provides robust, stable light collection. For the collection of elastically-scattered light, another immense advantage occurs—the background of scattered light is extremely low when using the flow-stream waveguide (FSW), because the same physical properties which confine the desired light within the stream also keep random scattered light out. In our studies, we have found that this new configuration gives the elastically-scattered RAS signal a much higher signal-to-noise ratio than that of forward scattered light.

Figure 3:
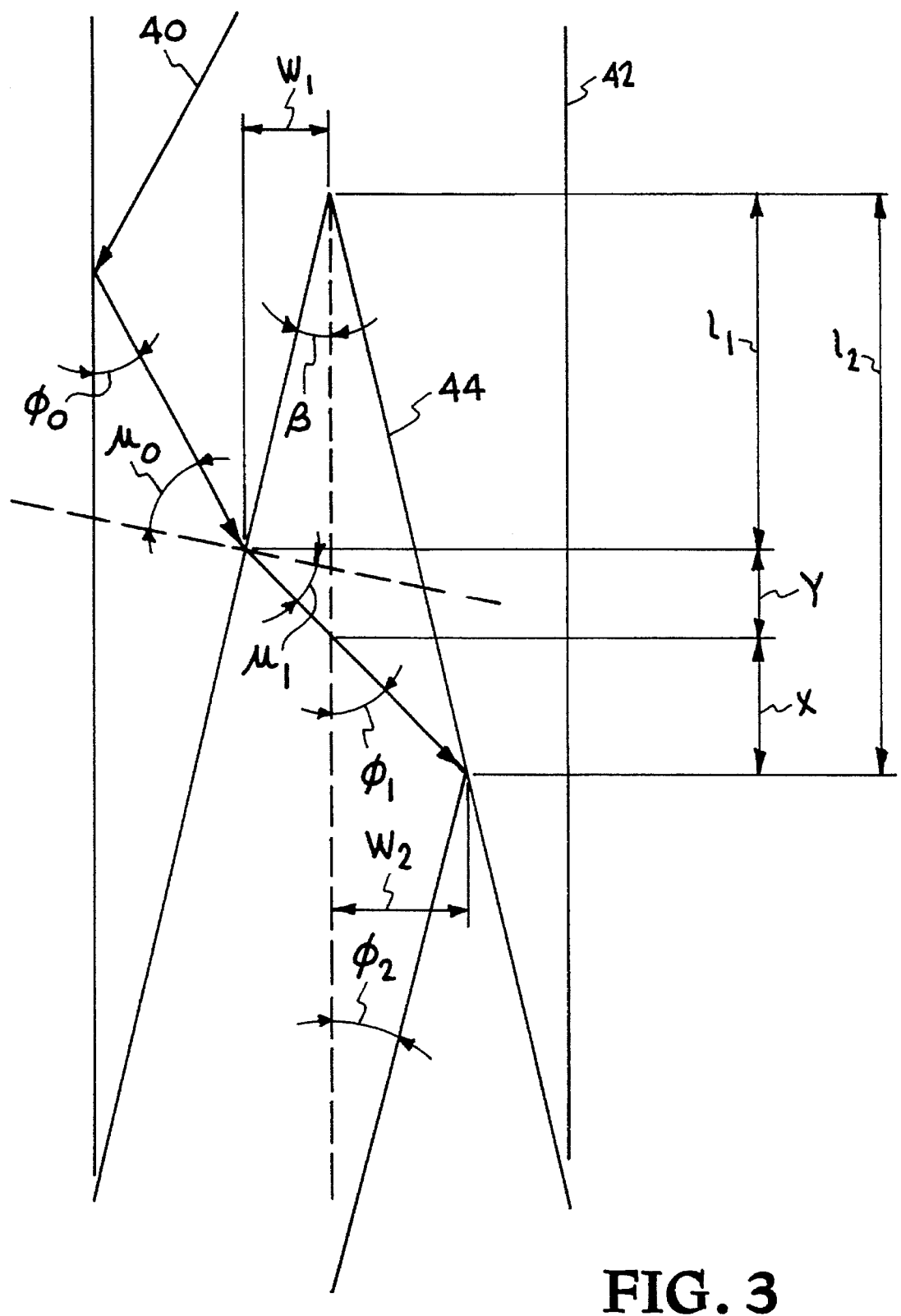
FIG. 3 is a schematic of the progress of a light ray as it passes from the aqueous flow stream into the conical fiber tip.

In building a system which uses the flow stream as an optical waveguide for collecting RAS light, one must take into consideration that the effective numerical aperture of a the water / air waveguide is $1/n_{water}=1/1.33=0.75$. One could place the light detector directly into the flow, possibly with a conical lens to keep the flow from becoming too unstable. In this case the area of the detector must be large enough to trap all of the rapidly diverging light from the terminus of the FSW. For our research purposes we found it convenient to place a conically-polished fiber-optic waveguide (FO) in the flow stream to serve as an intermediate optical device to conduct the light from the FSW to the light detector. (In this embodiment, it is easier to keep the flow stream from wetting the electrical contacts of the light detector). Because no commonly available fiber optic has 0.75 NA, some of the large-angle-of-propagation light in the FSW would not be confined in the FO. Therefore, it is necessary to expand the beam and reduce the NA of the propagating light as it enters the FO; thus, one must use a FO whose core is larger than the diameter of the flow stream. FIG. 3 shows the propagation of light ray 40 through aqueous carrier 42 and into a conically polished fiber tip 44 (silica).

In terms of ray tracing, by providing a conical taper at the transition from the FSW to the FO, the rays with $\square$ larger than the $\theta_{max}$, the maximum angle of propagation for the numerical aperture (NA) of the FO, reflect off the angled surfaces of the water film over the tip and are redirected down the FO with reduced propagation angles, $\square_2$. There is a refraction of any propagating light as it passes from the water, with index of refraction n=1.33 to the silica with n= 1.4. So, using Snell's Law, if half the tip angle is β, then as shown in FIG. 3, n1 sin(μ0)=n2 sin(μ1)

where μ0=90−$\square$0−β and $\square$1=90−μ1−β.

The minimum length of the tapered transition must be sufficiently large so that all propagating rays with $\square$>θ strike this slanted surface. The minimum length and width of the FO core can be estimated from:

tan $\square$1=w$_2$/x=w$_1$/y and tan β=w$_1$/l$_1$=w$_2$/l$_2$.

with l$_2$=x+y+l$_1$.
Thus, $$l_2 = w_1\{(\cot\beta + \cot\theta_1)/(1 - \tan\beta \cdot \cot\theta_1)\} \quad (1)$$

and, from above, $$w_2 = l_2 \cdot \tan\beta \quad (2)$$

For example, for 0.48-NA fiber with a 25° included tip angle ($2\beta$), $l_2$ and $w_2$ are $18.6 \cdot w_1$ and $4.1 \cdot w_1$, respectively, using the simple model shown in FIG. 3. Thus, for a 0.05-mm diameter flow stream, the 0.48-fiber core needs to be approximately 0.2 mm or larger in diameter. (The propagating rays which cause equations (1) and (2) to attain their maximum value for $l_2$, and $w_2$, as well, are those with $\theta_1$ only slightly larger than $\theta_{max}$.

Another important consideration in designing a tapered fiber to conduct RAS light from the flow stream waveguide (FSW) to a detector is the calculation of the included conical angle of the tip. As is shown in FIG. 3, the final angle of propagation $\theta_2$, assuming a thin film of water covering the silica core's tip, is given by $\theta_2 = |\theta_1 - 2\beta|$. In the preceding considerations, $\theta_1$ of the light rays has been modeled as either being less than $\theta_{max}$, and, thus, already being confined in the FO, or reflecting off of the conical taper once and being redirected down the FO with $\theta_2 < \theta_{max}$. (Because of the small difference in the indexes of refraction between water and silica, there is very little reflection from the tip's surface.) Although it may be counterintuitive, making the included tip angle $2\beta$ smaller makes the required FO core diameter smaller, until $|\theta_1 - 2\beta|$ becomes less than $\theta$. For the case of the 0.48-NA FO, the smallest $\beta$ that still provides $\theta_2 < \theta$ is 11.5°. Several 0.48-NA fiber tips were successfully polished to $\beta = 12.5°$. Using continuous wave (cw) diode lasers with power less than 10 mW, 1-Volt RAS pulses have been seen from 2.9-μm diameter latex spheres using inexpensive photodiode/preamp hybrids with 1 MΩ feedback resistor.

Figure 4A:
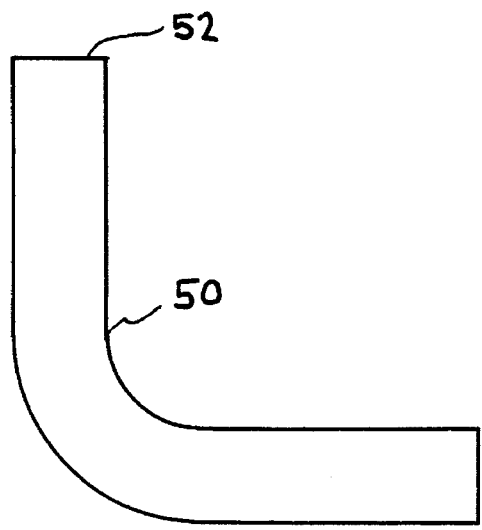
FIG. 4a is a fiber-optic with a flat termination.
Figure 4B:
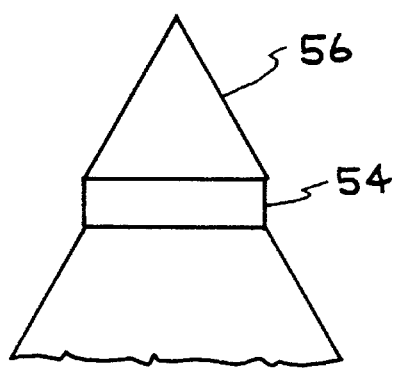
FIG. 4b is a photodetector with a conical lens.
Figure 4C:
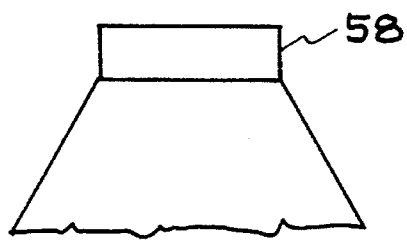
FIG. 4c is a photodetector without a lens.

FIG. 4a shows a fiber-optic 50 having an end 52 that has been polished flat. FIG. 4b shows a photodetector 54 with a conical lens 56 in aqueous carrier 12. FIG. 4c shows a photodetector 58 without a conical lens. Each of these elements can be substituted for the fiber-optic 26 of FIG. 2.

Changes and modifications in the specifically described embodiments can be carried out without departing from the scope of the invention, which is intended to be limited by the scope of the appended claims.

We claim:

1. A flow cytometer comprising:
   an orifice;
   an aqueous carrier which flows through said orifice, wherein said aqueous carrier forms an optical waveguide;
   means for inserting sample cells within said aqueous carrier;
   means for directing light through said aqueous carrier, wherein said light strikes said sample cells and thereby produces light scatter which propagates within said optical waveguide; and
   means for collecting said light scatter as it propagates within said optical waveguide.

2. The flow cytometer of claim 1, further comprising means for detecting said light scatter collected by said collecting means.

3. The flow cytometer of claim 2, wherein said detecting means comprises an optical filter/detector combination.

4. The flow cytometer of claim 2 wherein said collecting means comprise a fiber optic having a first face placed within said aqueous stream and a second face configured to provide light to said detecting means.

5. The flow cytometer of claim 4, wherein said first face is conically shaped.

6. The flow cytometer of claim 5, wherein said first face is conically shaped at 26°.

7. The flow cytometer of claim 4, wherein said second face is flat.

8. The flow cytometer of claim 4, wherein said fiber-optic has a 400-μm diameter core.

9. The flow cytometer of claim 4, wherein said fiber optic is formed of silica.

10. The flow cytometer of claim 1, further comprising a laser to produce said light.

11. The flow cytometer of claim 10, wherein said laser is selected from a group consisting of a diode laser, a solid state laser, a gas laser and a dye laser.

12. The flow cytometer of claim 10, wherein said laser is linearly polarized.

13. The flow cytometer of claim 1 wherein said collecting means comprise a photodetector placed within said aqueous stream.

14. The flow cytometer of claim 13, wherein said photodetector has a flat face.

15. The flow cytometer of claim 13, wherein said photodetector has a conical face.

16. The flow cytometer of claim 1, wherein said orifice has a 50-μm inside diameter.

17. The flow cytometer of claim 1, further comprising an arc lamp to produce said light.

18. A method for measuring light scatter in a flow cytometer, comprising:
   flowing an aqueous carrier through an orifice to form an optical waveguide;
   inserting sample cells within said aqueous carrier;
   directing a laser through said aqueous carrier, wherein said laser strikes said sample cells and thereby produces light scatter which propagates within said optical waveguide;
   collecting said light scatter propagating within said optical waveguide; and
   detecting said light scatter collected from within said optical waveguide.

* * * * *